(12) United States Patent
McLinden

(10) Patent No.: US 10,881,557 B1
(45) Date of Patent: Jan. 5, 2021

(54) SANITARY PRODUCT DISPOSAL DEVICE

(71) Applicant: Sheryl McLinden, Oviedo, FL (US)

(72) Inventor: Sheryl McLinden, Oviedo, FL (US)

( * ) Notice: Subject to any disclaimer, the term of this patent is extended or adjusted under 35 U.S.C. 154(b) by 365 days.

(21) Appl. No.: 15/958,544

(22) Filed: Apr. 20, 2018

(51) Int. Cl.
*A61F 13/551* (2006.01)
*A61F 13/84* (2006.01)
*B65D 33/16* (2006.01)

(52) U.S. Cl.
CPC ...... *A61F 13/5515* (2013.01); *A61F 13/8405* (2013.01); *A61F 2013/8414* (2013.01); *B65D 33/1608* (2013.01)

(58) Field of Classification Search
CPC .............. A61F 13/5515; A61F 13/5517; A61F 13/5518; B65D 33/1608
USPC ............ 206/438, 440, 812, 823; 604/385.02, 604/385.13
See application file for complete search history.

(56) References Cited

U.S. PATENT DOCUMENTS

| | | | | |
|---|---|---|---|---|
| 5,193,684 | A * | 3/1993 | McDonald | A61F 13/34 206/438 |
| 5,964,741 | A * | 10/1999 | Moder | A61F 13/55185 604/358 |
| 7,238,173 | B1 * | 7/2007 | Dobbs | A61F 13/5518 206/438 |
| 9,993,373 | B2 * | 6/2018 | Nassif | A61F 13/5518 |
| 10,568,783 | B2 * | 2/2020 | Mazor | B65F 1/00 |
| 2002/0188283 | A1 * | 12/2002 | Binner | A61F 13/266 604/385.13 |
| 2005/0098466 | A1 * | 5/2005 | Thomas | B65F 1/0006 206/440 |
| 2005/0121349 | A1 * | 6/2005 | Robert Hodges | A61F 13/55175 206/440 |
| 2005/0267432 | A1 * | 12/2005 | Sundberg | A61F 13/551 604/385.13 |
| 2006/0106358 | A1 * | 5/2006 | Hautop | B65F 1/10 604/385.13 |
| 2006/0212015 | A1 * | 9/2006 | Peele | A61F 15/003 604/385.13 |
| 2007/0083179 | A1 | 4/2007 | Fuentes | |
| 2009/0026101 | A1 * | 1/2009 | Hicks | B65F 1/0006 206/438 |
| 2009/0282786 | A1 | 11/2009 | Bland | |
| 2017/0007473 | A1 | 1/2017 | Germanow et al. | |
| 2020/0229993 | A1 * | 7/2020 | Bryant | B65F 1/16 |

* cited by examiner

*Primary Examiner* — Jacob K Ackun
(74) *Attorney, Agent, or Firm* — Allen Dyer Doppelt & Gilchrist, PA

(57) ABSTRACT

A sanitary product disposal device includes an outer telescopic member and a flexible inner liner for holding a sanitary product to be dispensed. The outer telescopic member is adjustable between a collapsed position and an expanded position. The telescopic member has two sealable ends. The inner liner has a dispensing end at one of the two sealable ends. The dispensing end of the liner is configured to receive a sanitary product. The telescopic member is in the collapsed position before receiving a sanitary product, and in the expanded position after receiving the sanitary product.

20 Claims, 8 Drawing Sheets

SANITARY PRODUCT DISPOSAL DEVICE

FIELD OF THE INVENTION

The present invention relates to a collection and disposal device, and more particularly, to a sanitary product collection and disposal device.

BACKGROUND OF THE INVENTION

Used sanitary products should be disposed in a proper and safe manner. Some channels of disposal are inappropriate. Disposal of a sanitary product directly in a sewage system can lead to blockage of the sewage. Wrapping a sanitary product in a wrapper or toilet paper and discarding it in a trash bin is possible, but it is often easy to tell that a sanitary product is being disposed of, which can cause embarrassment. In the disposal process, a user may have to touch a used sanitary product, causing hygiene concerns. It is desirable to provide a sanitary product disposal device that minimizes or eliminates the foresaid problems.

SUMMARY OF THE INVENTION

In view of the foregoing, it is an object of the present invention to provide a sanitary product disposal device. According to one embodiment of the present invention, a sanitary product disposal device includes an outer telescopic member and a flexible inner liner for holding a sanitary product to be dispensed. The outer telescopic member is adjustable between a collapsed position and an expanded position. The telescopic member has two sealable ends. The inner liner has a dispensing end at one of the two sealable ends. The dispensing end of the liner is configured to receive a sanitary product. The telescopic member is in the collapsed position before receiving a sanitary product, and in the expanded position after receiving the sanitary product.

According to another embodiment of the present invention, a method of disposing a sanitary product using the sanitary product disposal device includes receiving a sanitary product into the liner via the liner dispensing end. The sanitary product is moved into the telescopic member as the telescopic member extends from the collapsed position to the expanded position. The dispensing end of the liner is sealed, and the liner is positioned inside the telescopic member. The two ends of the telescopic member are sealed.

These and other objects, aspects and advantages of the present invention will be better appreciated in view of the drawings and following detailed description of preferred embodiments.

DETAILED DESCRIPTION OF PREFERRED EMBODIMENTS

Figure 1:
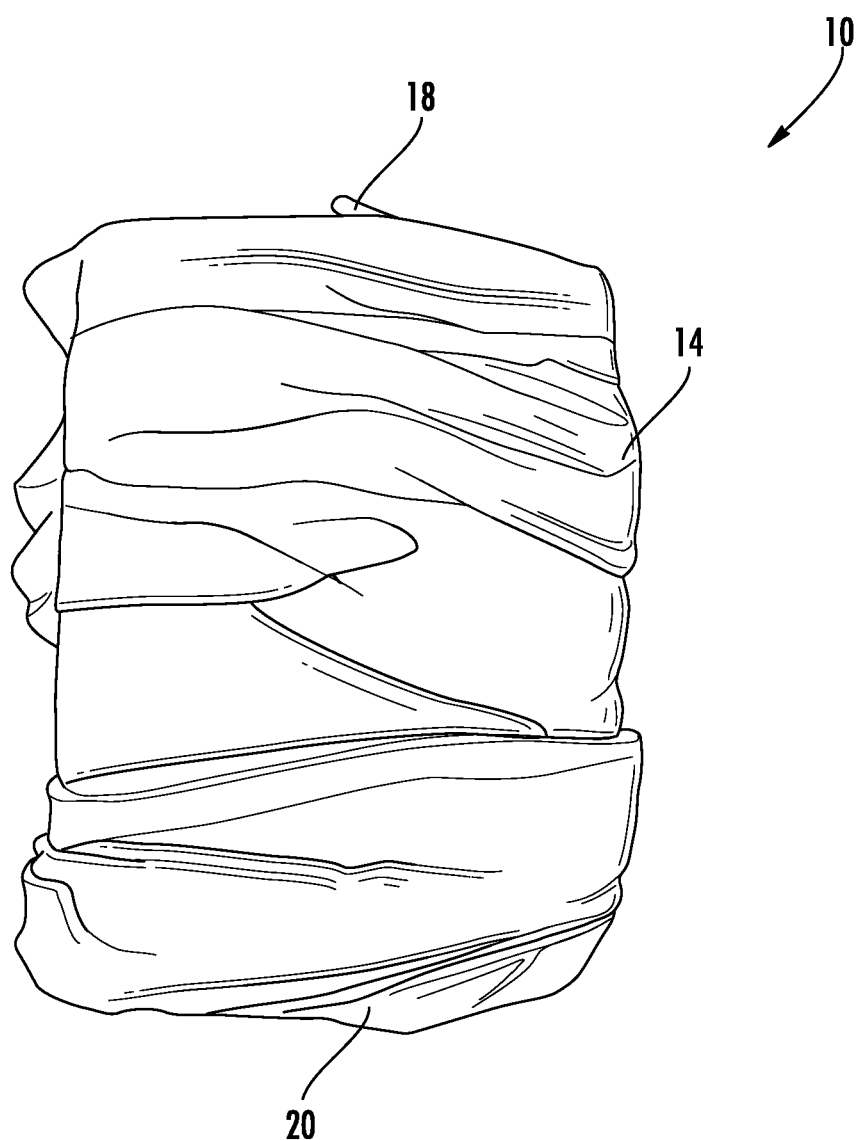
FIG. 1 is a side view of a sanitary product disposal device in a collapsed state, according to an embodiment of the present invention.
Figure 2:
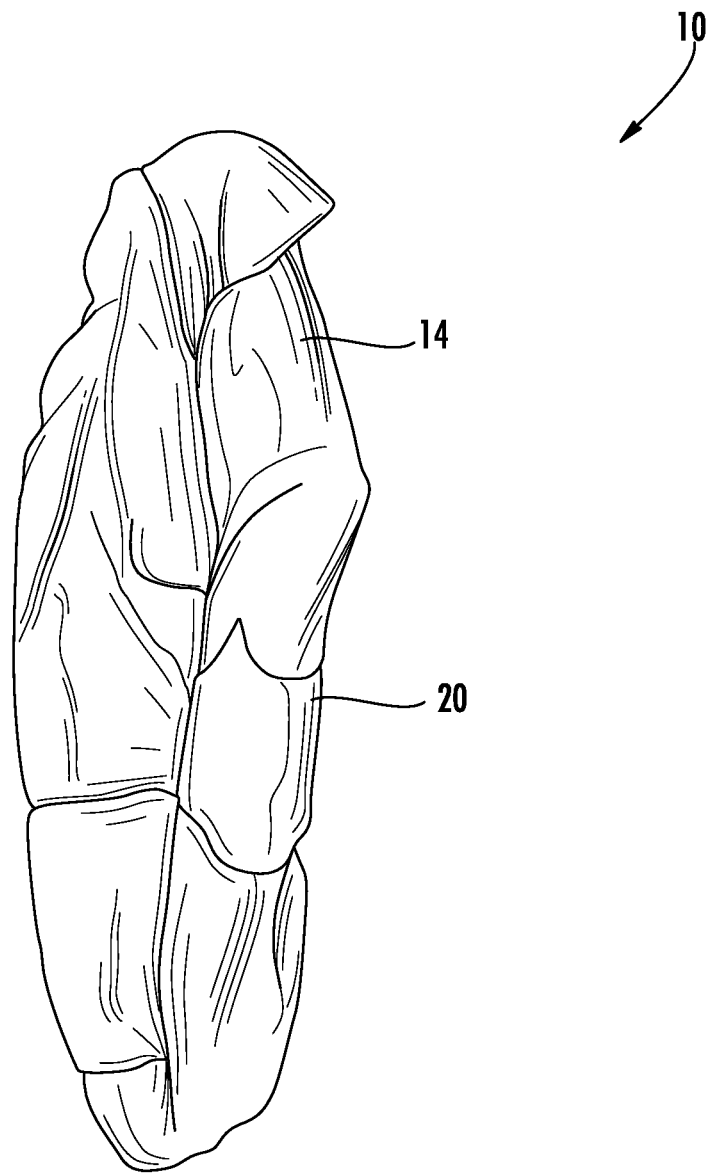
FIG. 2 is an end view of the sanitary product disposal device of FIG. 1 in the collapsed position.
Figure 3:
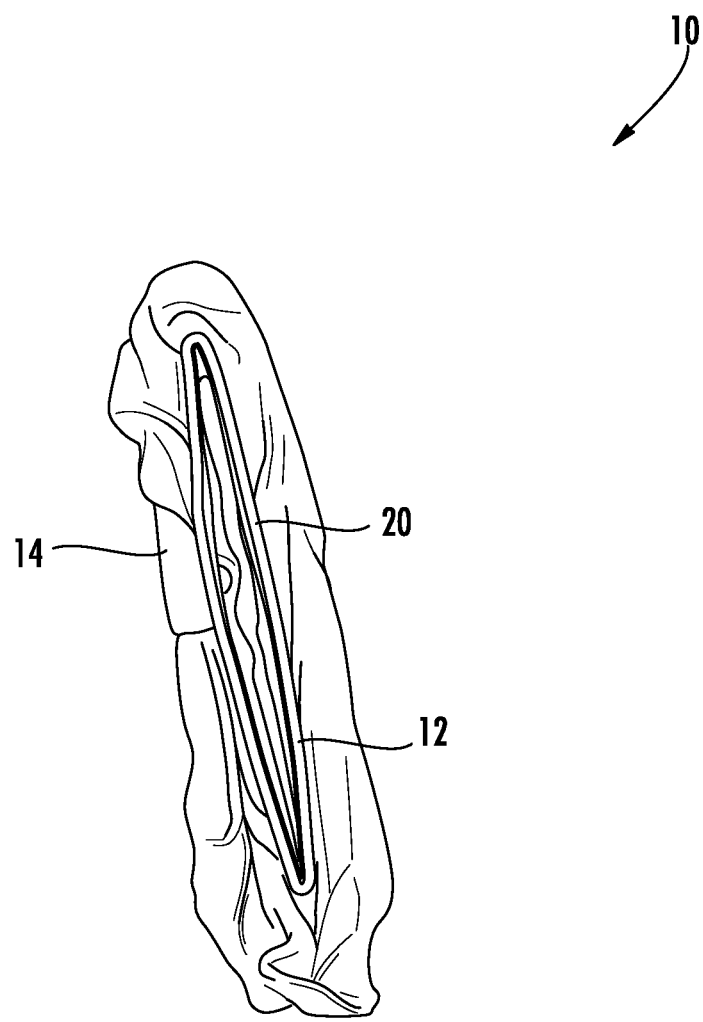
FIG. 3 is another end view of the sanitary product disposal device of FIG. 1 in the collapsed position.

Referring to FIGS. 1-7, a sanitary product disposal device 10 an outer telescopic member 12 and an inner liner 14 for holding a sanitary product to be dispensed. The telescopic member 14 is adjustable between a collapsed position (shown in FIGS. 1-3) and an expanded position (shown in FIGS. 4-7). FIGS. 1-3 show the liner 14 folded over the telescopic member 12 in the collapsed position. The decreased dimensions make the disposal device easy to carry and/or store.

The telescopic member 12 is dimensioned so as to be suitable for enclosing one or more sanitary products (e.g., one or more feminine products) intended for disposal. In the depicted embodiment, the telescopic member 12 has a plurality of cylindrical sections fitting into each other. The telescopic member can have a circular, rectangular, triangle, octagon, and hexagon or any other suitable cross-section. The telescopic member 12 has two sealable ends 18 and 20. The two ends 18 and 20 can be sealed via one or more of a flap, an adhesive tape, a button, a snap, a rib and groove fastener, a clip, buckle, clasp, a hook and loop fastener, a latch, and the like. Other suitable sealing means can be used.

The telescopic member 12 can have a color or a pattern of colors, and it can be imprinted with a design. The colors and/or patterns can further assist in concealment of contents enclosed therein. The telescopic member 12 is preferably opaque. The telescopic member 12 can be made of cardboard, paper, polymer and other stiff but light materials. The color and/or pattern of the telescopic member 12 can be made to match a user's purse or personal preferences. The telescopic member 12 can also be embedded with fragrance, scent, deodorant and/or antimicrobial agents. A sealed moist wipe (not shown) can be further attached to outer surface of the telescopic member 12 for additional cleaning. The telescopic member 12 is in the collapsed position before receiving a sanitary product and in the expanded position after receiving the sanitary product.

The inner liner 14 is dimensioned to be suitable for enclosing one or more sanitary products (e.g., one or more used feminine products). The inner liner 14 has a dispensing end 22 at one of the two sealable ends (e.g., sealable end 18), and a closed end 24 at the other sealable end 20. The dispensing end 22 of the liner 14 is configured to receive a sanitary product. The dispensing end 22 is sealed after receiving a sanitary product. The dispensing end 22 of the liner 14 can be sealable with adhesive tape, a rib and groove type fastener, a zip lock type fastener, and other suitable fasteners.

The inner liner 14 is made of non-permeable flexible material such as plastic. The liner 14 is preferably made of waterproof and biodegradable plastic material. The plastic material can have a color or a pattern of colors, and it can be imprinted with a design. The plastic material can also be embedded with fragrance, scent, deodorant and/or antimicrobial agents. The fragrance and antimicrobial agents can block and/or inhibit the growth of odor-causing bacteria on the sanitary produce enclosed therein. Absorbent material can be enclosed inside the liner 14 to absorb liquid as needed. At least a portion of a surface of the liner 14 can have a high friction property to facilitate grasping and/or pulling of a sanitary product if needed.

Referring to FIGS. 1-3, before receiving a sanitary product, the telescopic member 12 is in the collapsed position and the two sealable ends 22 and 24 are open. The liner 14 is folded over to the telescopic member 14 when the telescopic member 12 is in the collapsed position.

Figure 4:
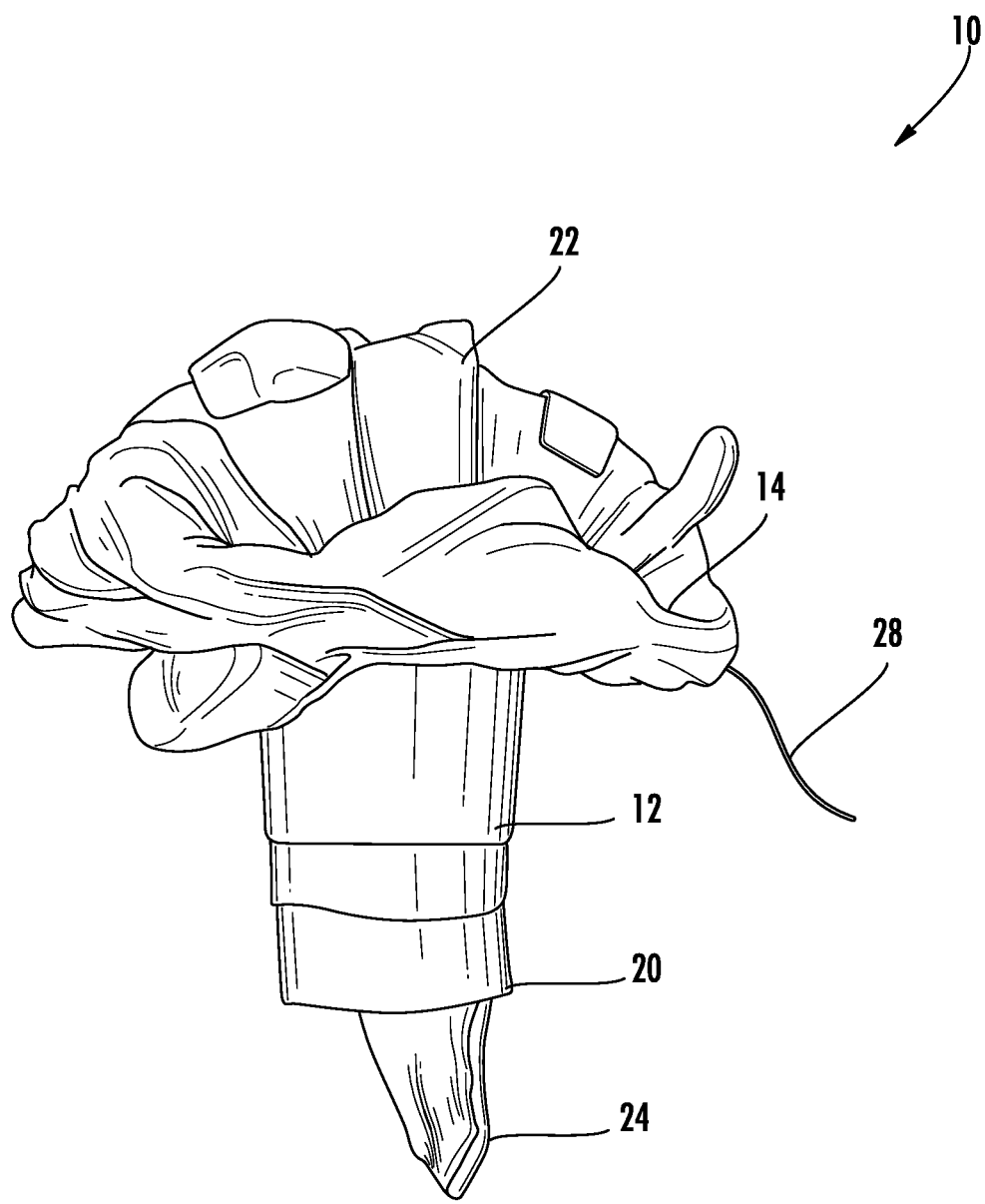
FIG. 4 is a perspective view of the sanitary product disposal device of FIG. 1 in an expanded position.
Figure 5:
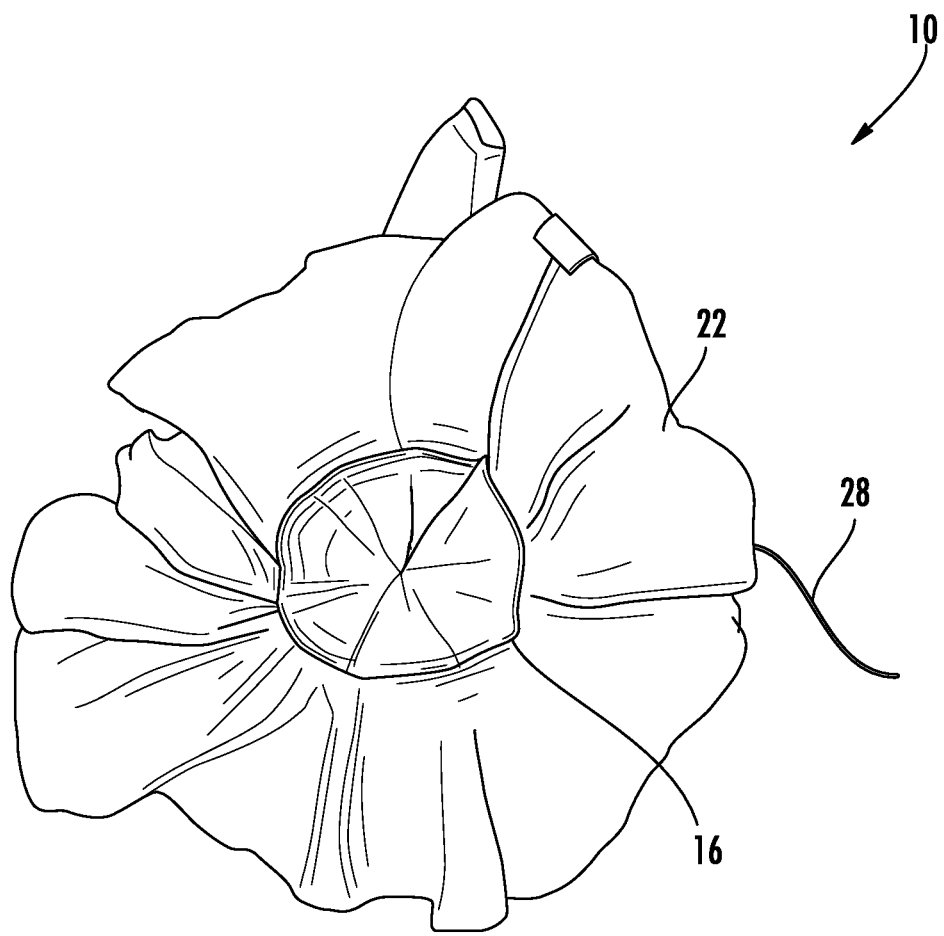
FIG. 5 is an end view of the sanitary product disposal device of FIG. 4 in the expanded position.

Referring to FIGS. 4-5, when receiving a sanitary product 16, the liner 14 is unfolded from the telescopic member 12 and is extended, such that the dispensing end 22 and the close end 24 of the liner 14 are outside of the telescopic member 12 for easy user access of the liner 14.

Figure 6:
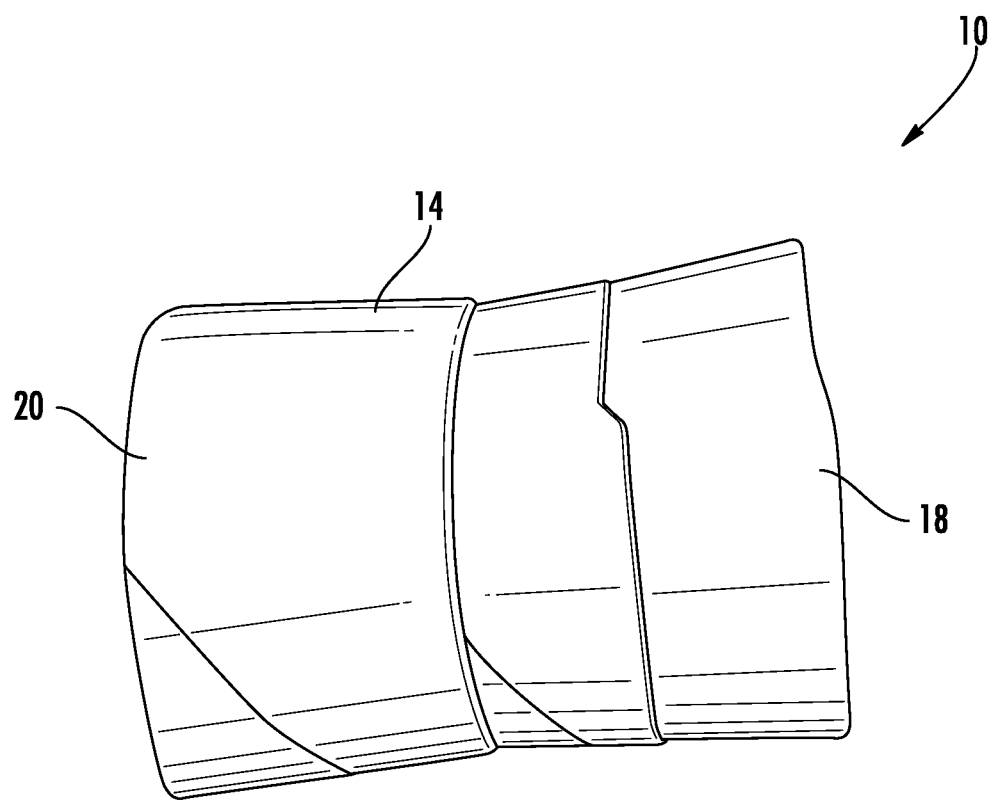
FIG. 6 is a side view of the sanitary product deposal device of FIG. 4.
Figure 7:
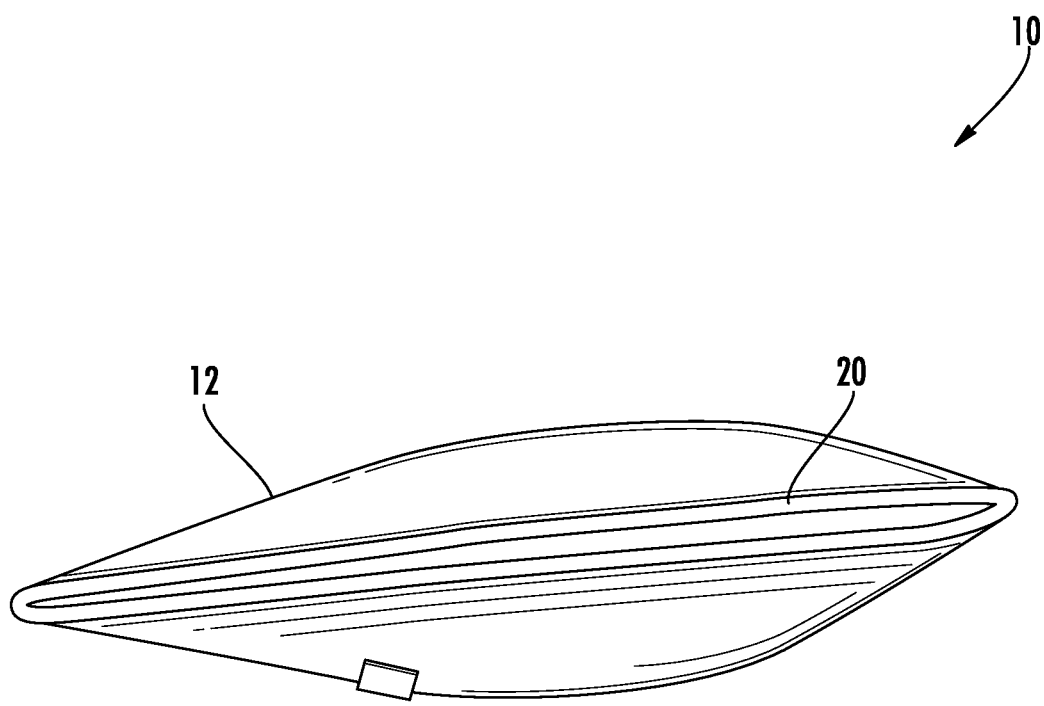
FIG. 7 is an end view of the sanitary product disposal device of FIG. 6 having two sealed ends.

Referring to FIGS. 6-7, after receiving a sanitary product, the sanitary product inside the liner 14 is positioned fully inside the telescopic member 12 and the telescopic member 12 is in the expanded position. The two sealable ends 18 and 20 are sealed before disposal, as shown in FIG. 7.

The sanitary product to be received and sealed in the disposal device 10 can include a used feminine hygiene product such as a tampon, an adult incontinence product, a condom, or any other individual product prefers hygienic and discreet disposal.

The sealed disposal device 10 can be placed within a general waste product basket, bin, or receptacle, without risking contact by user or cleaning personnel to see and touch the contents inside. The disposal device can also be used as sanitary product carriage device.

Figure 8:
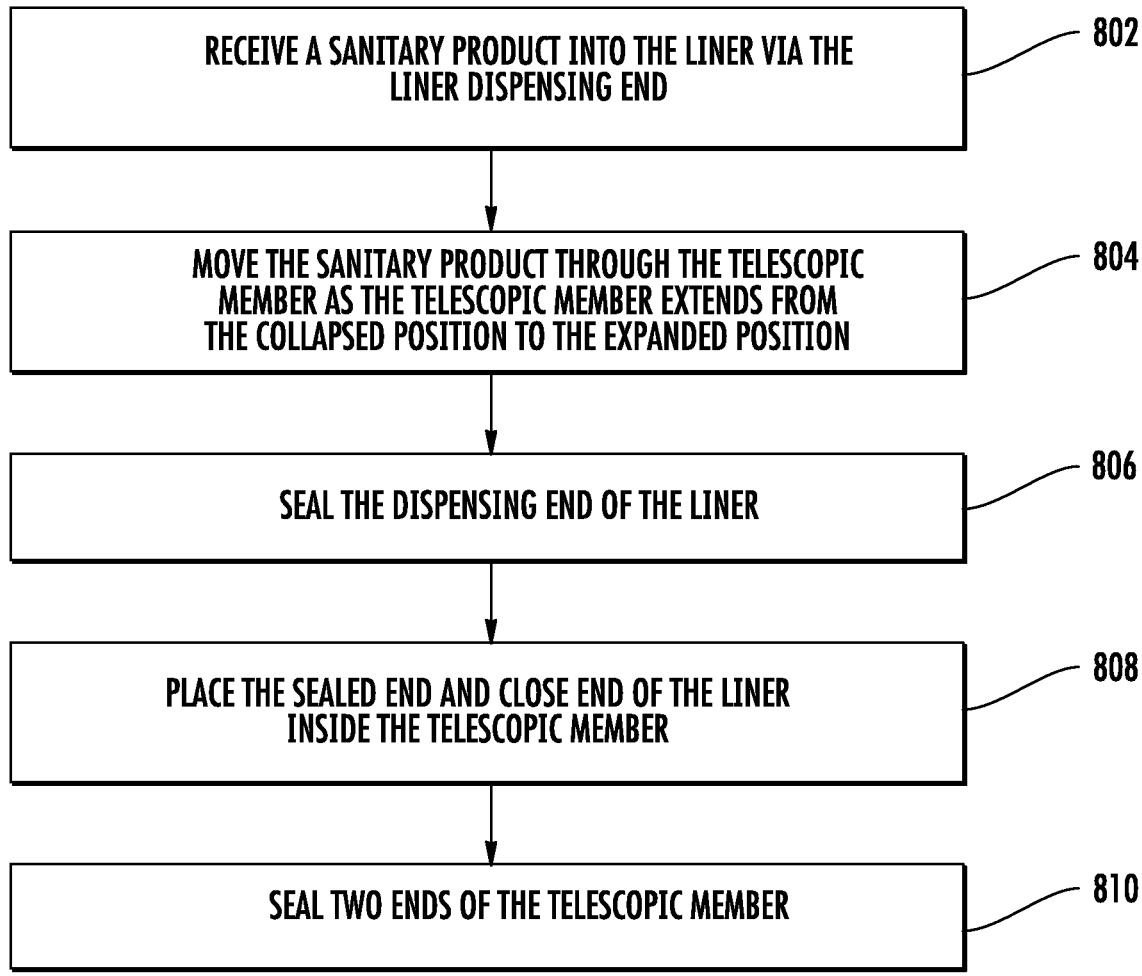
FIG. 8 is a flowchart of an example method of disposing sanitary produce using a sanitary disposal device.

Referring to FIG. 8, according to another embodiment of the present invention, a method of using the disposal device 10 to dispose a sanitary product includes, at step 802, receiving a sanitary product (e.g., a used feminine product) into the liner 14 via the liner dispensing end 22. A user hand can be positioned at outer surface of the liner close end 24 through the sealable end 20 and receive and/or hold the sanitary product. The liner 14 can prevent a user from coming in contact with a sanitary product.

At step 804, the sanitary product is moved into the telescopic member 12 as the telescopic member 12 extends from the collapsed position to the expanded position. For example, the user hand at the closed end 24 of the liner 14 can pull the sanitary product (e.g., sanitary product 16) through the telescopic member 12. The telescopic member 12 will then be in an expanded position when the sanitary product (e.g., a used feminine product) is completely positioned inside the expanded telescopic member 12.

At step 806, the dispensing end of the liner is sealed. For example, the liner 14 with the received sanitary product can be twisted and/or tied using a string (e.g. string 28). Other fastening methods can be used to seal the dispensing end 22. Other fastening methods can include an adhesive tape, a rib and groove type fastener, and a zip lock type fastener, and other suitable fastening method.

At step 808, the liner is placed inside the telescopic member. Specifically, the sealed dispensing end 22 of the liner 14 is pushed into one sealable end (e.g., end 18) of the telescopic member 12 and the other end (e.g., close end 24) of the liner 14 is pushed into the other sealable end (e.g., end 20) of the telescopic member 12. The string (e.g., string 28) attached to the dispensing end 22 of the liner 14 can also be used to pull the liner 14 into the telescopic member 12.

At step 810, two ends of the telescopic member are sealed. The two ends 18 and 20 of the telescopic member 12 can be sealed by an adhesive tape, a rib and groove type fastener, an enclosed zip lock, and other types of suitable fasteners. The sanitary product within the liner 14 thus becomes fully enclosed inside the telescopic member 12. The disposal device 10 can then be disposed of as appropriate, for instance, in a trash receptacle.

The foregoing is provided for illustrative and exemplary purposes; the present invention is not necessarily limited thereto. Rather, those skilled in the art will appreciate that various modifications, as well as adaptations to particular circumstances, are possible within the scope of the invention as herein shown and described and of the claims appended hereto.

What is claimed is:

1. A sanitary product disposal device comprising:
an outer telescopic member and a flexible inner liner for holding a sanitary product to be dispensed, the outer telescopic member being adjustable between a collapsed position and an expanded position;
wherein the telescopic member has two sealable ends, and the inner liner has a dispensing end at one of the two sealable ends, the dispensing end of the liner is configured to receive the sanitary product; and
wherein the telescopic member is in the collapsed position before receiving the sanitary product, and in the expanded position after receiving the sanitary product.

2. The disposal device of claim 1, wherein the telescopic member has a circular cross section.

3. The disposal device of claim 1, wherein the telescopic member has a rectangular cross section.

4. The disposal device of claim 1, wherein the liner is folded over to the telescopic member when the telescopic member is in the collapsed position.

5. The disposal device of claim 1, wherein the two sealable ends of the telescopic member are sealable via at least one of an adhesive tape, a rib and groove type fastener, and a zip lock type fastener.

6. The disposal device of claim 1, wherein the liner is made of non-permeable material.

7. The disposal device of claim 6, wherein the non-permeable material includes plastic material.

8. The disposal device of claim 1, wherein the telescopic member is opaque.

9. The disposal device of claim 1, wherein the telescopic member is made of paper.

10. The disposal device of claim 1, wherein the telescopic member is made with cardboard.

11. The disposal device of claim 1, wherein the sanitary product includes a used feminine hygiene product.

12. The disposal device of claim 1, the liner is embedded with at least one of fragrance and an antimicrobial agent.

13. The disposal device of claim 1, further comprising absorbent material enclosed inside the liner.

14. The disposal device of claim 1, further comprising a string attached to the dispensing end of the liner to pull the liner into the telescopic member.

15. A method of disposing a sanitary product using a sanitary product disposal device, the disposal device includes an outer telescopic member and an inner liner for holding a sanitary product to be dispensed, the telescopic member has two sealable ends, and the inner liner has a dispensing end at one of the two sealable ends, the dispensing end of the liner is configured to receive the sanitary product, the outer telescopic member is adjustable between a collapsed position and an expanded position, and the telescopic member is in the collapsed position before receiving a sanitary product, and in the expanded position after receiving the sanitary product, the method comprising:
receiving a sanitary product into the liner via the liner dispensing end;

moving the sanitary product into the telescopic member as the telescopic member extends from the collapsed position to the expanded position;
sealing the dispensing end of the liner;
placing the liner inside the telescopic member; and
sealing two sealable ends of the telescopic member.

16. The method of claim 15, wherein placing the liner inside the telescopic member includes pulling the dispensing end of the liner into the telescopic member via a string attached to the dispensing end of the liner.

17. The method of claim 15, wherein the dispensing end of the liner is sealed via at least one of an adhesive tape, a rib and groove type fastener, and a zip lock type fastener.

18. The method of claim 15, wherein the two sealable ends of the telescopic member are sealed via at least one of an adhesive tape, a rib and groove type fastener, and a zip lock type fastener.

19. The method of claim 15, further comprising disposing the sealed disposal device to a trash receptacle.

20. The method of claim 15, wherein the inner liner is made of plastic and the outer telescopic member is made of paper.

\* \* \* \* \*